United States Patent
Hasegawa (10) Patent No.: US 8,868,158 B2
(45) Date of Patent: Oct. 21, 2014

(54) OPTICAL ANALYZER

(75) Inventor: Takemi Hasegawa, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 12/858,087

(22) Filed: Aug. 17, 2010

(65) Prior Publication Data

US 2010/0331706 A1    Dec. 30, 2010

Related U.S. Application Data

(63) Continuation of application No. 11/921,577, filed as application No. PCT/JP2007/050672 on Jan. 18, 2007, now abandoned.

(30) Foreign Application Priority Data

Jan. 20, 2006    (JP) .................................. 2006-013010

(51) Int. Cl.
*A61B 6/00* (2006.01)
*B07C 5/342* (2006.01)
*A61B 5/00* (2006.01)
*G01N 21/65* (2006.01)
*G01N 21/35* (2014.01)

(52) U.S. Cl.
CPC .............. *G01N 21/65* (2013.01); *B07C 5/3425* (2013.01); *A61B 5/0059* (2013.01); *G01N 21/359* (2013.01)
USPC ........... 600/475; 356/479; 356/497; 356/456; 356/477

(58) Field of Classification Search
None
See application file for complete search history.

(56) References Cited

U.S. PATENT DOCUMENTS 5,553,615 A * 9/1996 Carim et al. .................. 600/324
5,960,146 A * 9/1999 Okuno et al. ................. 385/122

(Continued)

FOREIGN PATENT DOCUMENTS

JP    2002-005835 A    1/2002
JP    2005-515423      5/2005

(Continued)

OTHER PUBLICATIONS

N. Sugimoto et al., "Bismuth-based optical fiber with nonlinear coefficient of 1360 $W^{-1}km^{-1}$" in Optical Fiber Communication Conference, Technical Digest (CD) (Optical Society of America, 2004), paper PDP26.

(Continued)

*Primary Examiner* — Nicholas Evoy
(74) *Attorney, Agent, or Firm* — Venable LLP; Michael A. Sartori; Tamatane J. Aga (57) ABSTRACT

An optical analyzer performing analysis excellent in spatial resolution and in invasion depth is provided. The analyzer includes a diagnostic light source section including a seed light source which outputs seed light, and a silica optical fiber to which seed light is input and which generates diagnostic light having a HE11 mode field pattern utilizing a nonlinear optical phenomenon, an irradiation optical system converging the diagnostic light and irradiating a measurement subject with the diagnostic light, an acquisition optical system acquiring object light generated at the measurement subject, a spectrum measurement section receiving the object light and measuring a frequency spectrum of the object light, a storage section storing information of a frequency spectrum of a known substance, and an arithmetic section calculating a correspondence between the frequency spectrum of the object light and the frequency spectrum of the known substance, and analyzing the measurement subject based on the calculation result.

7 Claims, 8 Drawing Sheets

(56) References Cited

U.S. PATENT DOCUMENTS

| | | | |
|---|---|---|---|
| 6,043,927 A * | 3/2000 | Islam | 359/332 |
| 6,347,174 B1 * | 2/2002 | Onishi et al. | 385/122 |
| 6,352,502 B1 * | 3/2002 | Chaiken et al. | 600/473 |
| 6,421,164 B2 * | 7/2002 | Tearney et al. | 359/287 |
| 6,485,413 B1 * | 11/2002 | Boppart et al. | 600/160 |
| 6,577,884 B1 * | 6/2003 | Boas | 600/310 |
| 6,587,702 B1 | 7/2003 | Ruchti et al. | |
| 6,671,444 B1 * | 12/2003 | Arai et al. | 385/126 |
| 6,731,967 B1 * | 5/2004 | Turcott | 600/407 |
| 6,751,385 B2 * | 6/2004 | Futami et al. | 385/122 |
| 6,775,447 B2 * | 8/2004 | Nicholson et al. | 385/122 |
| 6,958,855 B2 * | 10/2005 | Kumar et al. | 359/330 |
| 7,148,970 B2 * | 12/2006 | de Boer | 356/479 |
| 7,355,716 B2 * | 4/2008 | de Boer et al. | 356/479 |
| 7,519,253 B2 * | 4/2009 | Islam | 385/122 |
| 7,567,349 B2 * | 7/2009 | Tearney et al. | 356/479 |
| 7,630,083 B2 * | 12/2009 | de Boer et al. | 356/479 |
| 7,643,152 B2 * | 1/2010 | de Boer et al. | 356/497 |
| 7,693,379 B2 * | 4/2010 | Imamura | 385/125 |
| 7,720,526 B1 * | 5/2010 | Modell | 600/476 |
| 8,055,108 B2 * | 11/2011 | Islam | 385/122 |
| 8,391,660 B2 * | 3/2013 | Islam | 385/122 |
| 2003/0147119 A1 | 8/2003 | Samson | |
| 2004/0021860 A1 | 2/2004 | Gardner et al. | |
| 2004/0125434 A1 * | 7/2004 | Kumar et al. | 359/330 |
| 2004/0127778 A1 | 7/2004 | Lambert et al. | |
| 2004/0150818 A1 * | 8/2004 | Armstrong et al. | 356/301 |
| 2004/0156572 A1 * | 8/2004 | Richardson et al. | 385/1 |
| 2004/0252300 A1 | 12/2004 | Slater | |
| 2004/0253365 A1 | 12/2004 | Warren et al. | |
| 2005/0047702 A1 * | 3/2005 | Parker et al. | 385/1 |
| 2005/0201432 A1 * | 9/2005 | Uehara et al. | 372/30 |
| 2005/0213907 A1 * | 9/2005 | Hiroishi et al. | 385/123 |
| 2005/0226575 A1 * | 10/2005 | Brown et al. | 385/122 |
| 2005/0226576 A1 * | 10/2005 | Feder et al. | 385/122 |
| 2006/0268393 A1 * | 11/2006 | Islam | 359/337.5 |
| 2007/0160091 A1 * | 7/2007 | Lee et al. | 372/6 |
| 2008/0045820 A1 * | 2/2008 | Rebec et al. | 600/316 |
| 2009/0028193 A1 * | 1/2009 | Islam | 372/6 |
| 2009/0073453 A1 * | 3/2009 | Hasegawa | 356/477 |
| 2009/0097810 A1 * | 4/2009 | Imamura | 385/125 |
| 2009/0204110 A1 * | 8/2009 | Islam | 606/9 |
| 2009/0209865 A1 * | 8/2009 | Hasegawa | 600/475 |
| 2012/0239013 A1 * | 9/2012 | Islam | 606/3 |

FOREIGN PATENT DOCUMENTS

| | | |
|---|---|---|
| JP | 2005-140794 A | 6/2005 |
| JP | 2005-195587 A | 7/2005 |
| JP | 2005-532547 | 10/2005 |
| JP | 2005-309415 A | 11/2005 |
| JP | 2005-345474 A | 12/2005 |
| WO | WO-03/060444 A1 | 7/2003 |
| WO | WO-2004/005871 A1 | 1/2004 |
| WO | WO-2005/022130 A1 | 3/2005 |

OTHER PUBLICATIONS

S.T. Sanders, "Wavelength-agile fiber laser using group-velocity dispersion of pulsed super-continua and application to broadband absorption spectroscopy," Applied Physics, vol. B75, Nov. 22, 2002, pp. 799-802.

Hideki Kano et al., "Femtosecond coherent anti-Stokes Raman scattering spectroscopy using supercontinuum generated from a photonic crystal fiber," Applied Physics Letters, vol. 85, No. 19, Nov. 8, 2004, pp. 4298-4300.

Extended European Search Report in European Patent Application No. 07706976.3, dated Nov. 5, 2013.

H. Kano et al., "Near-infrared coherent anti-Stokes Raman scattering microscopy using supercontinuum generated from a photonic crystal fiber," Applied Physics B, vol. B80, No. 2, pp. 243-246, 2005.

* cited by examiner

OPTICAL ANALYZER

This application claims priority to U.S. patent application Ser. No. 11/921,577 to Takemi Hasegawa, filed Dec. 5, 2007 entitled "Optical Analyzer," which is a National Stage Application of International Patent Application No. PCT/JP2007/050672, filed Jan. 18, 2007, which claims priority to Japanese Application No. 2006-013010, filed on Jan. 20, 2006, which has issued as Japanese Patent No. 3,992,064, the contents and subject matter of each being incorporated herein by reference.

TECHNICAL FIELD

The present invention relates to an optical analyzer capable of identifying a measurement subject and evaluating the state of a substance by measuring an optical spectrum, and of being preferably used for sorting medicine and for examining living tissue.

BACKGROUND ART

Examples of known optical analyzers capable of identifying measurement subjects and evaluating the states of substances are disclosed in Patent Documents 1 and 2. The optical analyzer disclosed in Patent Document 1 irradiates tissue with near-infrared radiation, measures an absorption spectrum, and determines the kind of fat in adipose tissue in accordance with the absorption spectrum, so as to measure the characteristic of the tissue and classify the tissue. The analysis using this optical analyzer may result in a low signal-to-noise ratio and a low spatial resolution. The optical analyzer disclosed in Patent Document 2 irradiates a measurement subject with pulse light with a wavelength of 1.06 μm output from a Nd:YAG pulse laser source so as to excite Raman scattering, and synchronously detect Raman scattering light using a photo detector. This optical analyzer may result in a small invasion depth when measuring a measurement subject with a large elastic scattering.

Patent Document 1: U.S. Pat. No. 6,587,702
Patent Document 2: Japanese Unexamined Patent Application Publication No. 2002-005835

DISCLOSURE OF INVENTION

Problems to be Solved by the Invention

An object of the present invention is to provide an optical analyzer capable of performing analysis excellent in spatial resolution and in invasion depth.

Means for Solving the Problems

To attain the object, an optical analyzer is provided which includes (1) a diagnostic light source section including a seed light source, and a silica optical fiber to which seed light is input and which generates diagnostic light having a HE11 mode field pattern utilizing a nonlinear optical phenomenon and outputs the diagnostic light, (2) an irradiation optical system which converges the diagnostic light and irradiates a measurement subject with the diagnostic light, (3) an acquisition optical system which acquires object light generated at the measurement subject because of the irradiation with the diagnostic light, (4) a spectrum measurement section which receives the object light and measures a frequency spectrum of the object light, (5) a storage section which stores information of a frequency spectrum of a known substance, and (6) an arithmetic section which calculates a correspondence between the frequency spectrum of the object light and the frequency spectrum of the known substance, and analyzes the measurement subject based on the calculation result. Preferably, a spatial density of an optical power may be 1 mW/μm² or more at least at a part of the optical fiber of the diagnostic light source section, and the diagnostic light source section may output the diagnostic light having an optical power of 1 μW/nm or more at least in a part of a spectrum band from 0.8 to 3.0 μm.

According to a first aspect of the optical analyzer of the present invention, the seed light source of the diagnostic light source section includes a pump pulse source. In the diagnostic light source section, a spectrum of pump pulse light output from the pump pulse source is expanded utilizing the nonlinear optical effect during propagation in the optical fiber so that the pump pulse light is output as the diagnostic light. The acquisition optical system acquires, as the object light, diagnostic light having a loss generated at the measurement subject because of the irradiation with the diagnostic light. The frequency spectrum of the known substance is a loss spectrum. The arithmetic section calculates a correspondence between the frequency spectrum of the object light and the loss spectrum, and analyzes the measurement subject based on the calculation result.

According to a second aspect of the optical analyzer of the present invention, the seed light source of the diagnostic light source section includes a seed pulse source and a pump source. In the diagnostic light source section, pump light output from the pump source is input to the optical fiber so as to generate an optical parametric gain in the optical fiber, and seed pulse light output from the seed pulse source is optically amplified using the optical parametric gain in the optical fiber and output as the diagnostic light. A center wavelength of the diagnostic light is within a wavelength range from 1400 to 1800 nm. The acquisition optical system acquires, as the object light, Raman scattering light generated at the measurement subject because of the irradiation with the diagnostic light. The frequency spectrum of the known substance is a Raman scattering spectrum. The arithmetic section calculates a correspondence between the frequency spectrum of the object light and the Raman scattering spectrum, and analyzes the measurement subject based on the calculation result.

According to a third aspect of the optical analyzer of the present invention, the seed light source of the diagnostic light source section includes a seed pulse source, a pump source, and a pump pulse source. In the diagnostic light source section, pump light output from the pump source is input to the optical fiber so as to generate an optical parametric gain in the optical fiber, and seed pulse light output from the seed pulse source is optically amplified using the optical parametric gain in the optical fiber and output as first diagnostic light. A spectrum of pump pulse light output from the pump pulse source is expanded utilizing the nonlinear optical effect during propagation in the optical fiber so that the pump pulse light is output as second diagnostic light. A center wavelength of the first diagnostic light is within a wavelength range from 1400 to 1800 nm. The acquisition optical system acquires, as first object light, Raman scattering light generated at the measurement subject because of the irradiation with the first diagnostic light, and also acquires, as second object light, second diagnostic light having a loss generated at the measurement subject because of the irradiation with the second diagnostic light. The frequency spectrum of the known substance contains a Raman scattering spectrum and a loss spectrum. The arithmetic section calculates a correspondence between the frequency spectrum of the first object light and the Raman scattering spectrum, calculates a correspondence between the frequency spectrum of the second object light and the loss spectrum, and analyzes the measurement subject based on the calculation results.

In addition, a medicine sorting method is provided which includes using the optical analyzer of the present invention, measuring a spatial distribution of physiologically active molecules contained in medicine as a measurement subject, and determining whether the spatial distribution is conformed with a predetermined specification.

Further, a tissue examination method is provided which includes using the optical analyzer of the present invention, irradiating living tissue as a measurement subject with diagnostic light with a wavelength within a wavelength range from 1.6 to 1.8 µm, and measuring a spatial distribution of physiologically active molecules contained in the measurement subject. Preferably in the tissue examination method, information of the frequency spectrum of the known substance may be information of a spectrum of an undifferentiated embryonic stem cell, and the undifferentiated embryonic stem cell contained in the measurement subject may be detected.

Advantages

With the present invention, analysis excellent in spatial resolution and in invasion depth can be performed.

REFERENCE NUMERALS 1 to 4, 5A, 5B, 6A, 6B, 7: optical analyzer, 9: measurement subject, 10: diagnostic light source section, 11: pump pulse source, 12: seed pulse source, 13: pump source, 14: optical fiber, 15$a$, 15$b$: semi-transparent mirror, 16: lens, 17: semi-transparent mirror, 18: optical filter, 20: optical system, 21$a$, 21$b$: semi-transparent mirror, 22: fixed mirror, 23: movable mirror, 24: lens, 30: spectrum measurement section, 31$a$, 31$b$, 31$c$: spectroscope, 32: subtracter, 33: processor, 40: storage section, 50: arithmetic section, 60: display section

BEST MODE FOR CARRYING OUT THE INVENTION

Embodiments of the present invention are described below with reference to the drawings. The drawings are provided merely for description, and do not limit the scope of the invention. In the drawings, similar numerals refer similar portions to avoid redundant descriptions. The ratios illustrated in the drawings may not be necessarily correct.

First Embodiment of Optical Analyzer

Figure 1:
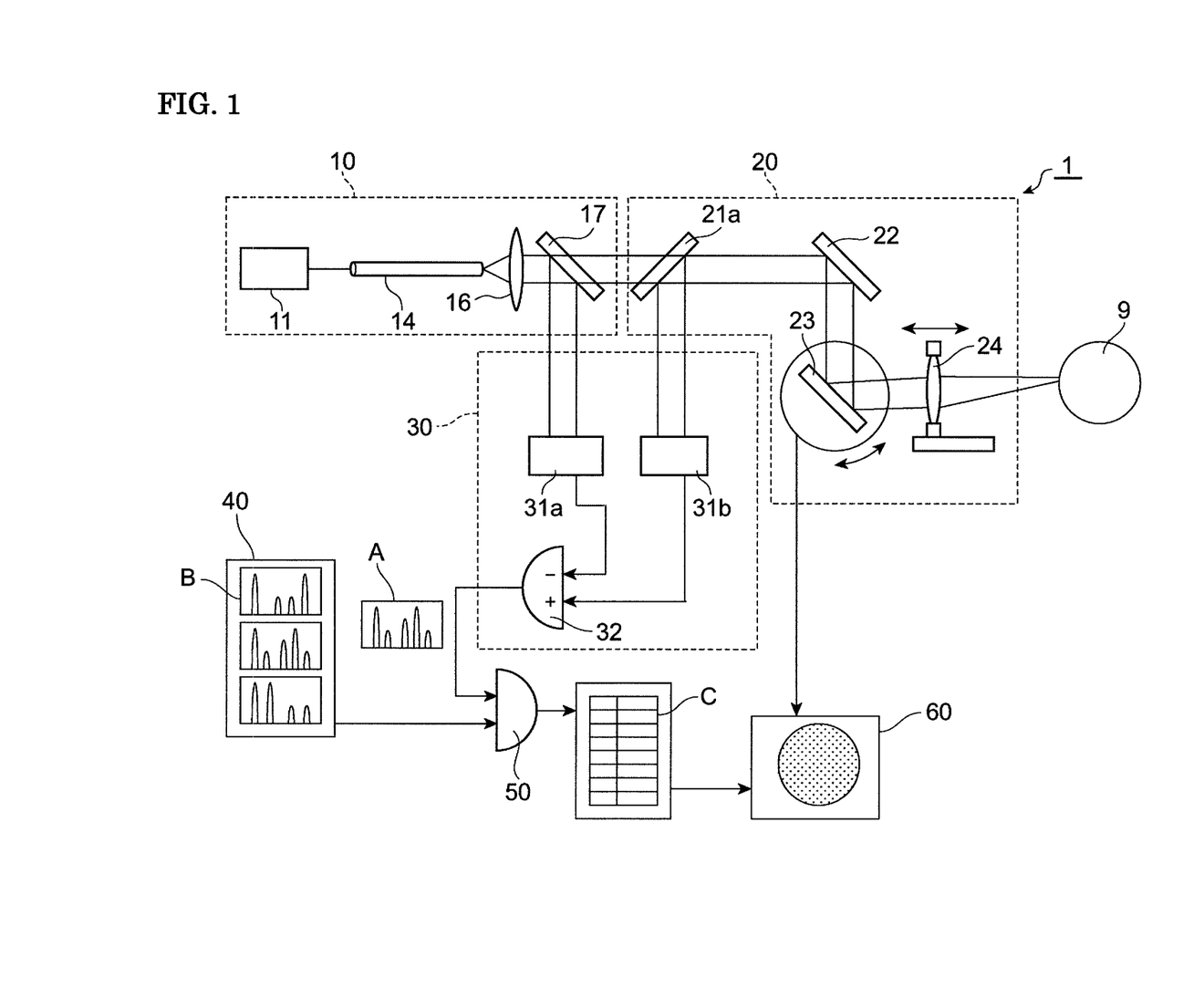
FIG. 1 is a block diagram showing a first embodiment of an optical analyzer of the present invention.

FIG. 1 is a block diagram showing a first embodiment of an optical analyzer of the present invention. An optical analyzer 1 is a device capable of identifying a measurement subject 9 and evaluating the state of a substance by measuring a loss spectrum. The optical analyzer 1 includes a diagnostic light source section 10, an optical system 20, a spectrum measurement section 30, a storage section 40, an arithmetic section 50, and a display section 60.

The diagnostic light source section 10 includes a pump pulse source 11, an optical fiber 14, a lens 16, and a semi-transparent mirror 17. A spatial density of an optical power of at least a part of the optical fiber 14 is 1 mW/µm$^2$ or more. The diagnostic light source section 10 outputs diagnostic light having an optical power of 1 µW/nm or more at least in a part of a spectrum band ranging from 0.8 to 3.0 µm.

The pump pulse source 11 generates pump pulse light having a center wavelength λp within a wavelength range from 1530 to 1620 nm (more preferably, a wavelength range from 1530 to 1560 nm), and outputs the pump pulse light. The silica optical fiber 14, in the case of the wavelength λp, has a nonlinear coefficient γ of 20 [W$^{-1}$km$^-$] or more (a measurement value obtained by cross-phase modulation, Optics Lett., Vol. 20, 1995, pp. 988), and an absolute value of a chromatic dispersion slope of 0.05 [ps/nm$^2$/km] or less. The pump pulse light output from the pump pulse source 11 as a seed light source enters one end of the optical fiber 14, and is coupled to the HE11 mode of the optical fiber 14.

Utilizing a nonlinear optical effect in the optical fiber 14, the spectrum of the pump pulse light is expanded, and thus, broadband light which is known as supercontinuum light (SC light) is generated in the optical fiber 14. The SC light has a power spectrum density of 1 [µW/nm] or more in a wavelength range from 800 to 3000 nm. The wavelength range and spectrum density of the SC light generated in the optical fiber 14 are variable in accordance with the power and wavelength of the pump pulse light input to the optical fiber 14. The SC light may have a power spectrum density of 10 [µW/nm] in a wavelength range from 1000 to 2000 nm. The SC light has an electric field distribution of the HE11 mode of the optical fiber.

The SC light dispersed and output from the other end of the optical fiber 14 is input to the lens 16, and the lens 16 collimates the SC light. The semi-transparent mirror 17 splits the SC light collimated by the lens 16 into two parts. The semi-transparent mirror 17 outputs a part of the SC light to the optical system 20, and outputs the residual part of the SC light to the spectrum measurement section 30. The SC light output from the diagnostic light source section 10 as described above becomes diagnostic light which is emitted on the measurement subject 9. The power of the diagnostic light varies with time in synchronization with variation in the power of the pump pulse light output from the pump pulse source 11.

The optical system 20 serves as an irradiation optical system which converges the diagnostic light output from the diagnostic light source section 10 and irradiates the measurement subject 9 with the diagnostic light, and also serves as an acquisition optical system which acquires object light generated at the measurement subject 9 because of the irradiation of the measurement subject 9 with the diagnostic light. The optical system 20 includes a semi-transparent mirror 21$a$, a fixed mirror 22, a movable mirror 23, and a lens 24. The diagnostic light output from the diagnostic light source section 10 passes through the semi-transparent mirror 21a, is reflected by the fixed mirror 22 and then the movable mirror 23, is converged by the lens 24, and is emitted to a part of the measurement subject 9. The irradiation region of the diagnostic light on the measurement subject 9 may be two-dimensionally varied by the movable mirror 23 in directions orthogonal to the light axis, and also, the region may be varied in the light-axis direction in accordance with the position of the lens 24. The diameter of the irradiation region of the diagnostic light on the measurement subject 9 may be within a range from 1 µm to 1 mm, by properly selecting the kind and position of the lens 24.

A part of the diagnostic light output from the diagnostic light source section 10 is extracted by the semi-transparent mirror 17, and input to the spectrum measurement section 30. Also, a part of the object light from the measurement subject 9 passes the lens 24, the movable mirror 23, the fixed mirror 22 and the semi-transparent mirror 21a, and then is input to the spectrum measurement section 30.

The spectrum measurement section 30 receives the object light acquired by the optical system 20, and measures a frequency spectrum of the object light. The spectrum measurement section 30 includes spectroscopes 31a and 31b, and a subtracter 32. The spectroscope 31a receives the diagnostic light extracted by the semi-transparent mirror 17 of the diagnostic light source section 10, and measures a power spectrum of this diagnostic light. The spectroscope 31b receives the object light from the semi-transparent mirror 21a, and measures a power spectrum of the object light.

The spectroscopes 31a and 31b may be devices such as monochromoters, variable filters, configurations using dispersion media and detector arrays, or Fourier transform spectroscopes. In particular, the configurations using the dispersion media and the detector arrays provide high light-utilization efficiency as compared with the configurations using filters, thereby measuring the frequency components thereof at the same time. The spectroscopes 31a and 31b measure the power spectrum of the object light and the power spectrum of the diagnostic light at the same time. The subtracter 32 subtracts the power spectrum of the object light from the power spectrum of the diagnostic light on a log scale, so as to obtain a loss spectrum A of the measurement subject 9.

The storage section 40 stores information of loss spectra B of various known substances. The arithmetic section 50 reads out the information of the loss spectra B from the storage section 40 one by one, and calculates a correspondence between the loss spectrum A obtained by the spectrum measurement section 30 and each of the loss spectra B. A table C for the substances and their correspondences is created, and a substance having the highest degree of correspondence is selected, thereby identifying the substance contained in the measurement subject 9. Also, a combination of the loss spectra of a plurality of known substances may be compared with the loss spectrum A, and its correspondence may be calculated so as to obtain a proportion of the known substances contained in the measurement subject 9. The display section 60 assigns different colors to the substances, and displays the colors in a manner superposed on an image of the measurement subject 9. Accordingly, a user may recognize a substance distribution of the measurement subject 9.

With the first embodiment, since the diagnostic light (the SC light) has the electric field distribution of the HE11 mode of the optical fiber 14, a diameter of the converged light on the measurement subject 9 may become as small as 1 µm at a minimum. In addition, since the wavelength of the diagnostic light (the SC light) is as long as 800 nm or more, information of a deep portion can be obtained even when the measurement subject 9 has a large scattering coefficient.

Second Embodiment of Optical Analyzer

Figure 2:
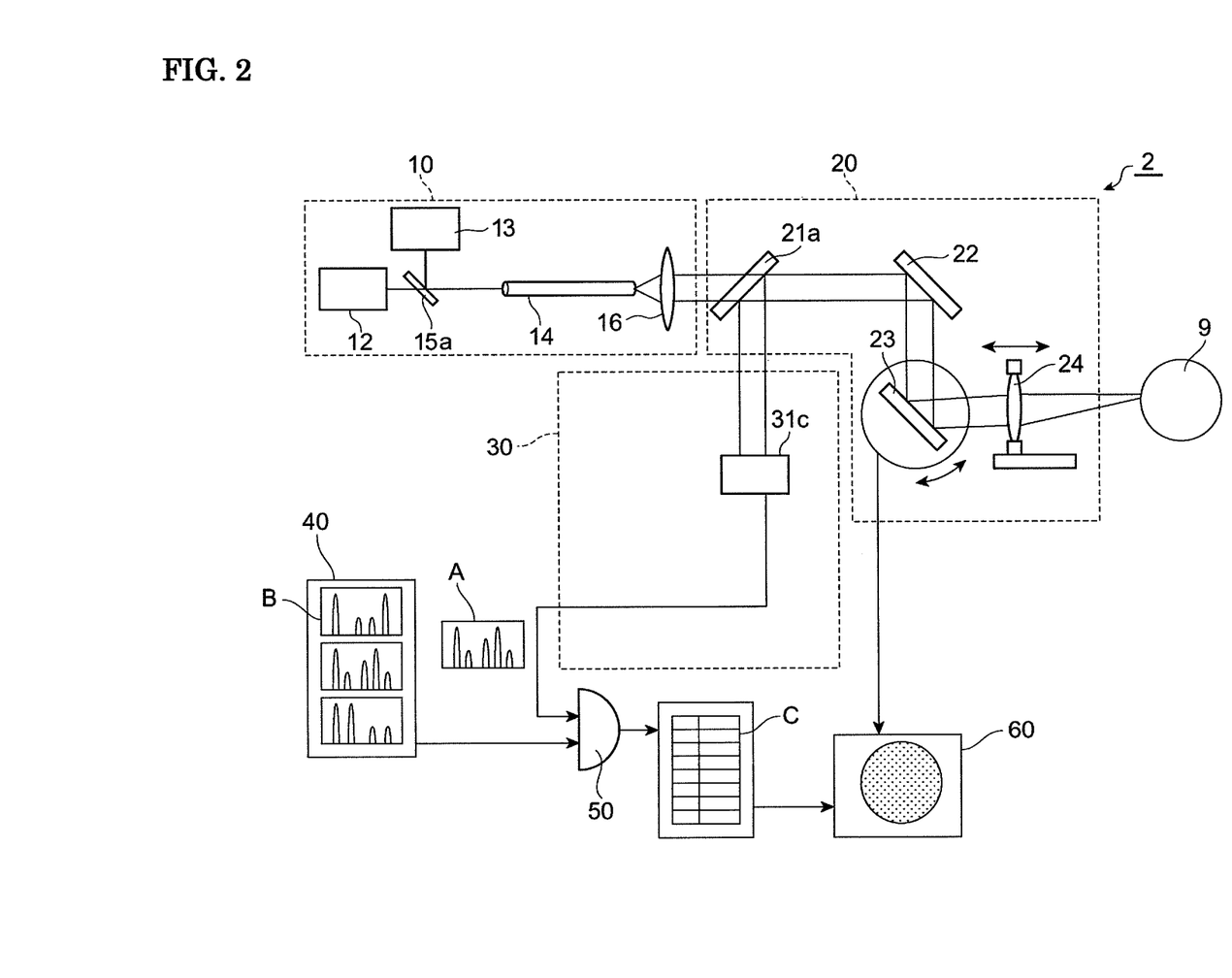
FIG. 2 is a block diagram showing a second embodiment of the optical analyzer of the present invention.

FIG. 2 is a block diagram showing a second embodiment of the optical analyzer of the present invention. An optical analyzer 2 is a device capable of identifying a measurement subject 9 and evaluating the state of a substance by measuring a Raman scattering spectrum. The optical analyzer 2 includes a diagnostic light source section 10, an optical system 20, a spectrum measurement section 30, a storage section 40, an arithmetic section 50, and a display section 60.

The diagnostic light source section 10 generates and outputs diagnostic light. The diagnostic light source section 10 includes a seed pulse source 12, a pump source 13, an optical fiber 14, a semi-transparent mirror 15a, and a lens 16. The seed pulse source 12 generates seed pulse light having a center wavelength $\lambda s$ within a wavelength range from 1400 to 1800 nm (more preferably, a wavelength range from 1580 to 1650 nm). The pump source 13 generates pump light having a center wavelength $\lambda p$ in a wavelength range from 1530 to 1580 nm (more preferably, a wavelength range of 1580 nm).

The pump light output from the pump source 13 is in the form of CW or pulse. The pump light output from the pump source 13 in the form of pulse can provide an advantage that a large parametric gain can be obtained using a high peak power if the seed pulse light and the pump pulse light are temporarily synchronized. On the other hand, the pump light output from the pump source 13 in the form of CW can provide an advantage that the device can be simplified because the synchronization with the seed pulse light is not necessary.

The optical fiber 14, in the case of the wavelength $\lambda p$, has a nonlinear coefficient $\gamma$ of 20 $[W^{-1}km^{-1}]$ or more, an absolute value of a chromatic dispersion slope of 0.05 $[ps/nm^2/km]$ or less, and a $\beta^{(4)}$ (a fourth-order derivative of a propagation constant in accordance with an angular frequency) of $1 \times 10^{-55}$ $[s^2/m]$ or less.

The wavelength $\lambda p$ of the pump light output from the pump source 13 is selected such that a group velocity of the seed pulse light corresponds to that of the pump CW light in the optical fiber 14. The seed pulse light and the pump CW light are coupled by the semi-transparent mirror 15a, and then coupled to the HE11 mode of the optical fiber 14. Because of the nonlinear optical effect in the optical fiber 14, the seed pulse light is amplified with the gain of the optical parametric amplification (OPA), and thus, the pulse light with the wavelength $\lambda s$ having a power of about 10 mW can be generated. The pulse light emitted from the optical fiber 14 is collimated by the lens 16, and output as the diagnostic light from the diagnostic light source section 10. The diagnostic light has an electric field distribution of the HE11 mode of the optical fiber 14.

The optical system 20 is similar to that of the first embodiment. The diagnostic light output from the diagnostic light source section 10 passes through the semi-transparent mirror 21a, is reflected by the fixed mirror 22 and then the movable mirror 23, is converged by the lens 24, and is emitted to a part of the measurement subject 9. An irradiation region of the diagnostic light on the measurement subject 9 may be two-dimensionally varied by the movable mirror 23 in directions orthogonal to the light axis, and also, the region may be varied in the light-axis direction in accordance with the position of the lens 24. Raman scattering has a feature that it is generated if the power density exceeds a threshold value. Therefore, the Raman scattering light can be selectively generated at a desired position of the measurement subject by setting the focal position of the lens 24 at a desired position in the light-axis direction and in the directions orthogonal to the light axis. Using the Raman scattering, the measurement subject can be three-dimensionally analyzed.

The object light (the Raman scattering light) from the measurement subject 9 passes the lens 24, the movable mirror 23, the fixed mirror 22 and the semi-transparent mirror 21a, and then is input to the spectrum measurement section 30. The spectrum measurement section 30 receives the object light acquired by the optical system 20, and measures a Raman scattering spectrum of the object light. The spectrum measurement section 30 includes a spectroscope 31c. The spectroscope 31c receives the object light (the Raman scattering light) from the semi-transparent mirror 21a, and measures the power spectrum (the Raman scattering spectrum) of the object light. The spectroscope 31c may be a device such as a monochrometer, a variable filter, a configuration using a dispersion medium and a detector array, or a Fourier transform spectroscope. In particular, the configuration using the dispersion medium and the detector array provides high light-utilization efficiency as compared with the configuration using a filter, thereby measuring the frequency components thereof at the same time.

The storage section 40 stores information of Raman scattering spectra B of various known substances. The arithmetic section 50 reads out the information of the Raman scattering spectra B from the storage section 40 one by one, and calculates a correspondence between the Raman scattering spectrum A obtained by the spectrum measurement section 30 and each of the Raman scattering spectra B. A table C for the substances and their correspondences is created, and a substance having the highest degree of correspondence is selected, thereby identifying the substance contained in the measurement subject 9. Also, a combination of the Raman scattering spectra of a plurality of known substances may be compared with the Raman scattering spectrum A, and a correspondence may be calculated so as to obtain a proportion of the known substances contained in the measurement subject 9. The display section 60 assigns different colors to the substances, and displays the colors in a manner superposed on an image of the measurement subject 9. Accordingly, a user may recognize the substance distribution in the measurement subject 9.

In the second embodiment, the optical fiber 14 has a nonlinear coefficient of 20 $[W^{-1}km^{-1}]$ or more, a chromatic dispersion slope of a small absolute value of 0.05 $[ps/nm^2/km]$ or less, and a $\beta^{(4)}$ of a small absolute value of $1\times10^{-55}$ $[s^2/m]$ or less. As a result, a parametric gain with a wide bandwidth such as from 100 to 300 nm can be generated. Accordingly, diagnostic light with a wavelength ranging from 1600 to 1700 nm in which transmittances in water is larger than in other wavelengths therearound can be generated, by using the pump light with wavelengths of around 1550 nm where a high power source can be utilized.

Also, since the diagnostic light has the electric field distribution of the HE11 mode of the optical fiber 14, a diameter of the converged light on the measurement subject 9 may become as small as 1 μm at a minimum. In addition, since the wavelength of the diagnostic light is as long as 1400 nm or more, information of a deep portion can be obtained even when the measurement subject 9 has a large scattering coefficient. At this time, as compared with the related art using pump light with a wavelength shorter than 1200 nm, fluorescence can be prevented, and a signal-to-noise ratio of the Raman scattering measurement can be improved.

Third Embodiment of Optical Analyzer

Figure 3:
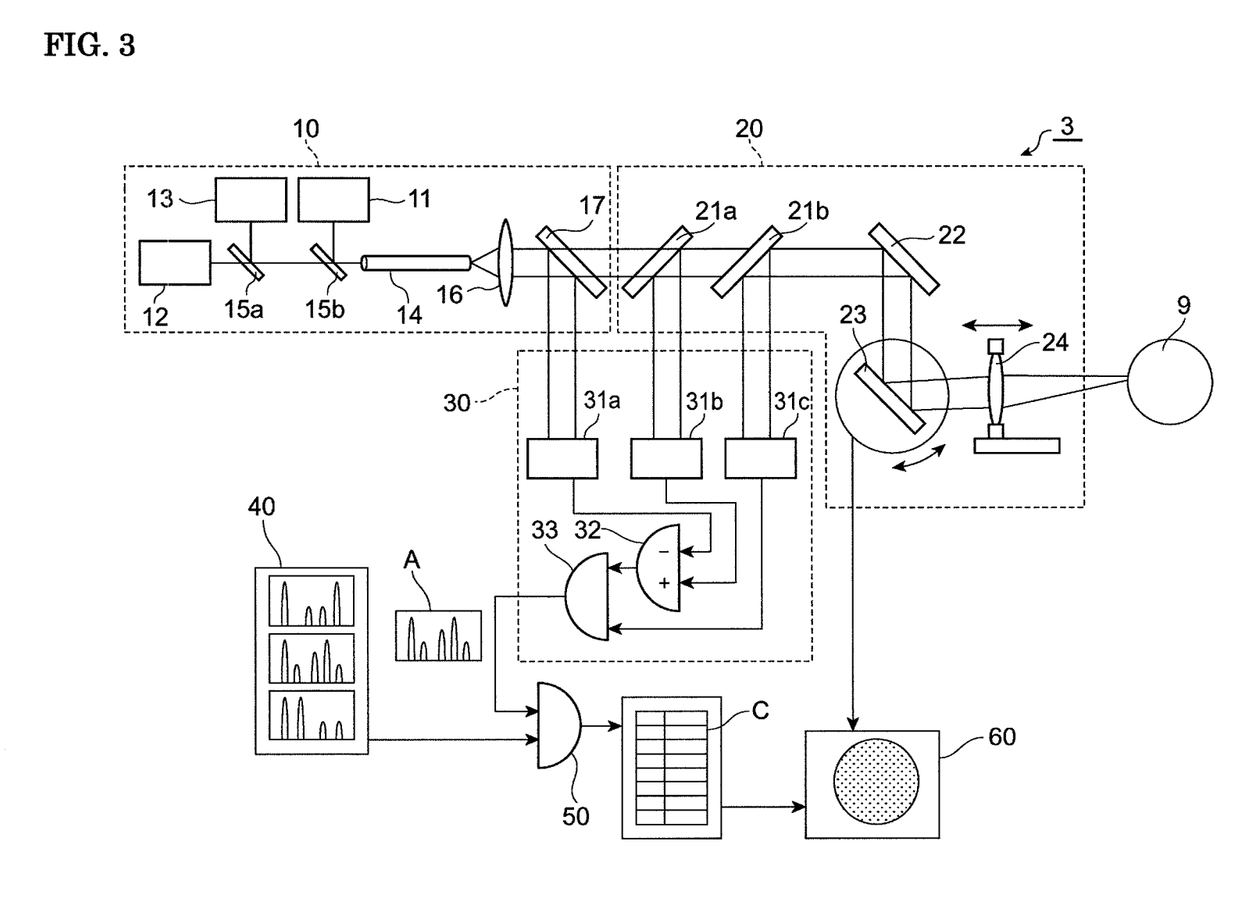
FIG. 3 is a block diagram showing a third embodiment of the optical analyzer of the present invention.

FIG. 3 is a block diagram showing a third embodiment of the optical analyzer of the present invention. An optical analyzer 3 is a device capable of identifying a measurement subject 9 and evaluating the state of a substance by measuring a loss spectrum and a Raman scattering spectrum. The optical analyzer 2 includes a diagnostic light source section 10, an optical system 20, a spectrum measurement section 30, a storage section 40, an arithmetic section 50, and a display section 60.

The diagnostic light source section 10 generates and outputs first diagnostic light and second diagnostic light. The diagnostic light source section 10 includes a pump pulse source 11, a seed pulse source 12, a pump source 13, an optical fiber 14, semi-transparent mirrors 15a and 15b, a lens 16, and a semi-transparent mirror 17. In these elements, the pump pulse source 11 is similar to that of the first embodiment, and the seed pulse source 12 and the pump source 13 are similar to those of the second embodiment. The optical fiber 14 is similar to that of the second embodiment, and the lens 16 and the semi-transparent mirror 17 are similar to those of the first embodiment.

The semi-transparent mirrors 15a and 15b couple the pump pulse light output from the pump pulse source 11, the seed pulse light output from the seed pulse source 12, and the pump light output from the pump source 13. The coupled light enters the one end of the optical fiber 14, and is coupled to the HE11 mode of the optical fiber 14.

The pump light output from the pump source 13 is input to the optical fiber 14, so that the optical parametric gain is generated in the optical fiber 14. The seed pulse light output from the seed pulse source 12 is also input to the optical fiber 14, the seed pulse light is optically amplified because of the optical parametric gain in the optical fiber 14, and the optically amplified seed pulse light is output as the first diagnostic light. In addition, the pump pulse light output from the pump pulse source 11 is input to the optical fiber 14, the spectrum is expanded utilizing the nonlinear optical effect generated during the propagation of the optical fiber 14, and the pump pulse light (the SC light) with the expanded spectrum is output as the second diagnostic light.

The optical system 20 serves as an irradiation optical system which converges the diagnostic light output from the diagnostic light source section 10 and irradiates the measurement subject 9 with the diagnostic light, and also serves as an acquisition optical system which acquires object light generated at the measurement subject 9 because of the irradiation of the measurement subject 9 with the diagnostic light. The optical system 20 includes semi-transparent mirrors 21a and 21b, a fixed mirror 22, a movable mirror 23, and a lens 24. The first diagnostic light and the second diagnostic light output from the diagnostic light source section 10 pass through the semi-transparent mirrors 21a and 21b, are reflected by the fixed mirror 22 and then the movable mirror 23, are converged by the lens 24, and are emitted to a part of the measurement subject 9. The irradiation region of the first diagnostic light and that of the second diagnostic light on the measurement subject 9 may be two-dimensionally varied by the movable mirror 23 in directions orthogonal to the light axis, and also, the regions may be varied in the light-axis direction in accordance with the position of the lens 24. The diameters of the irradiation region of the first diagnostic light and that of the second diagnostic light on the measurement subject 9 may be within a range from 1 µm to 1 mm, by properly selecting the kind and position of the lens 24.

At the measurement subject 9, Raman scattering light is generated because of the irradiation with the first diagnostic light, and second object light is generated from second diagnostic light having a loss generated at the measurement subject 9 because of the irradiation with the second diagnostic light. The first object light (the Raman scattering light) from the measurement subject 9 passes the lens 24, the movable mirror 23, the fixed mirror 22 and the semi-transparent mirror 21b, and then is input to the spectrum measurement section 30. The second object light (the second diagnostic light having the loss) from the measurement subject 9 passes the lens 24, the movable mirror 23, the fixed mirror 22 and the semi-transparent mirrors 21b and 21a, and then is input to the spectrum measurement section 30.

The spectrum measurement section 30 receives the first object light and the second object light acquired by the optical system 20, and measures the frequency spectrum of each object light. The spectrum measurement section 30 includes spectroscopes 31a, 31b and 31c, a subtracter 32, and a processor 33. The spectroscope 31a receives the diagnostic light extracted by the semi-transparent mirror 17 of the diagnostic light source section 10, and measures a power spectrum of the diagnostic light. The spectroscope 31b receives the second object light (the second diagnostic light having the loss) from the semi-transparent mirror 21a, and measures a power spectrum of the second object light. The spectroscope 31c receives the first object light (the Raman scattering light) from the semi-transparent mirror 21b, and measures a power spectrum (a Raman scattering spectrum) of the first object light.

The spectroscopes 31a, 31b and 31c may be devices such as monochrometers, variable filters, configurations using dispersion media and detector arrays, or Fourier transform spectroscopes. In particular, the configurations using the dispersion media and the detector arrays provide high light-utilization efficiency as compared with the configurations using filters, thereby measuring the frequency components thereof at the same time. The spectroscopes 31a and 31b measure the power spectrum of the second object light and the power spectrum of the second diagnostic light at the same time. The subtracter 32 subtracts the power spectrum of the second object light from the power spectrum of the second diagnostic light on a log scale, so as to obtain a loss spectrum of the measurement subject 9. The Raman scattering spectrum obtained by the spectroscope 31c and the loss spectrum obtained by the subtracter 32 are measured at the same time, and output from the processor 33 as a data set.

The storage section 40 stores information of data sets of loss spectra and Raman scattering spectra of various known substances. The arithmetic section 50 reads out the information of the Raman scattering spectra from the storage section 40 one by one, and calculates a correspondence between each of the Raman scattering spectra and the frequency spectrum of the first object light measured by the spectrum measurement section 30. The arithmetic section 50 reads out the information of the loss spectra from the storage section 40 one by one, and calculates a correspondence between each of the loss spectra and the frequency spectrum of the second object light measured by the spectrum measurement section 30. Then the arithmetic section 50 creates a table for the substances and their correspondences, and a substance having the highest degree of correspondence is selected, thereby identifying the substance contained in the measurement subject 9. The display section 60 assigns different colors to the substances, and displays the colors in a manner superposed on an image of the measurement subject 9. Accordingly, a user may recognize a substance distribution in the measurement subject 9.

In the third embodiment, the optical fiber 14 has a large nonlinear coefficient of 20 $[W^{-1}km^{-1}]$ or more, a chromatic dispersion slope of a small absolute value of 0.05 $[ps/nm^2/km]$ or less, and a $\beta^{(4)}$ of a small absolute value of $1\times10^{-55}$ $[s^2/m]$ or less. As a result, the second diagnostic light (the SC light) for the loss spectrum measurement and the first diagnostic light (the pump pulse) for the Raman measurement can be generated at the same time, thereby collecting information relating to the measurement subject 9 from various perspectives, and improving an identification accuracy. As compared with measuring the loss spectrum and the Raman spectrum separately, error factors such as a temporal fluctuation of a measurement system and a measurement subject, and a variation in a convergence position of the diagnostic light, can be reduced.

For the measurement of the loss spectrum, since the second diagnostic light (the SC light) has the electric field distribution of the HE11 mode of the optical fiber 14, the diameter of the converged light on the measurement subject 9 may become as small as 1 µm at a minimum. In addition, since the wavelength of the second diagnostic light (the SC light) is as long as 800 nm or more, information of a deep portion can be obtained even when the measurement subject 9 has a large scattering coefficient.

In the measurement of the Raman spectrum, the first diagnostic light in a wavelength ranging from 1600 to 1700 nm in which transmittances in water is larger than with the other wavelength therearound can be generated, by using pump light with wavelengths of around 1550 nm where a high power source can be utilized. Also, since the first diagnostic light has the electric field distribution of the HE11 mode of the optical fiber 14, a diameter of the converged light on the measurement subject 9 may become as small as 1 µm at a minimum. In addition, since the wavelength of the first diagnostic light is as long as 1400 nm or more, information of a deep portion can be obtained even when the measurement subject 9 has a large scattering coefficient. At this time, as compared with the related art using a pump with a wavelength shorter than 1200 nm, fluorescence can be prevented, and a signal-to-noise ratio of the Raman scattering measurement can be improved.

Fourth Embodiment of Optical Analyzer

Figure 4:
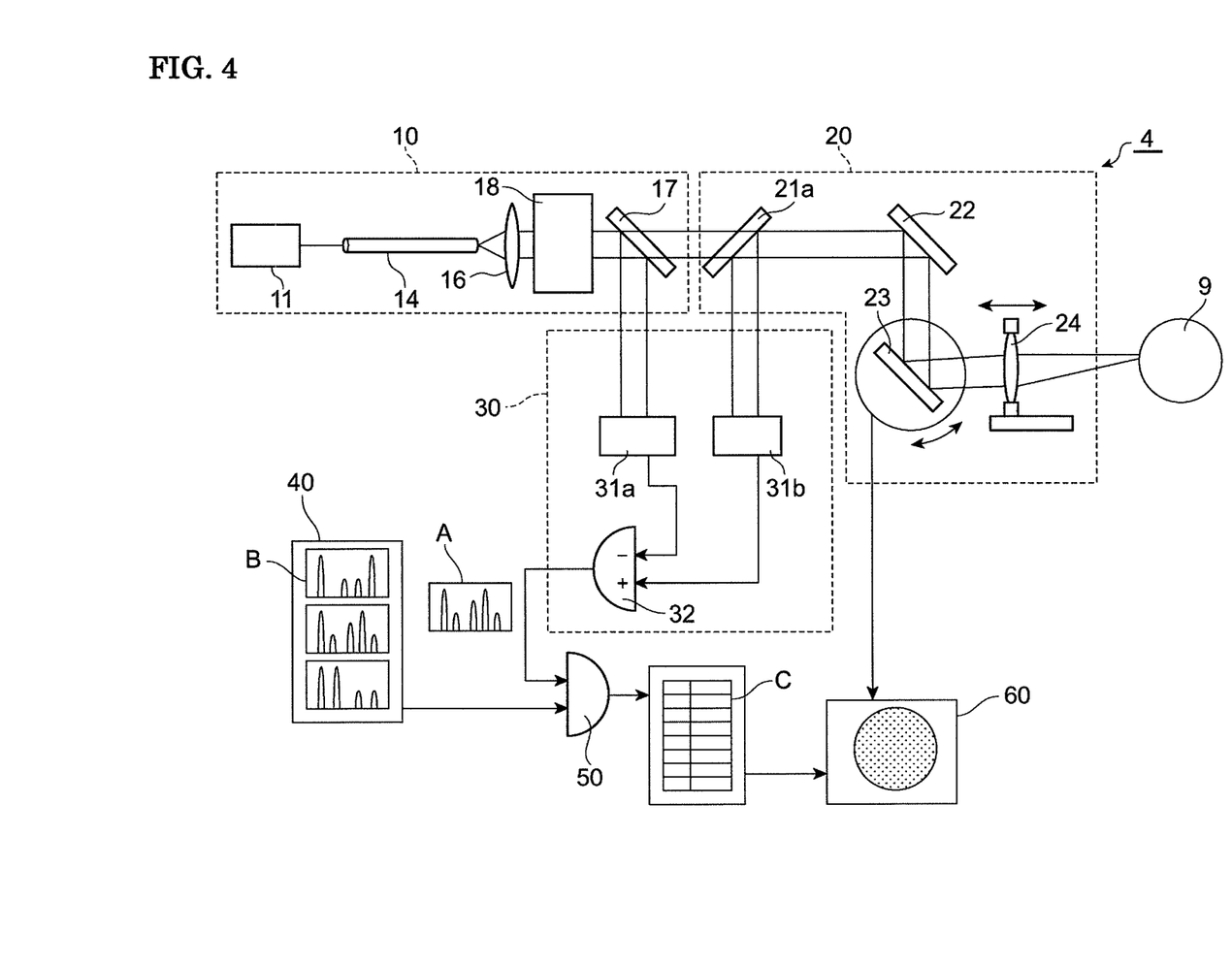
FIG. 4 is a block diagram showing a fourth embodiment of the optical analyzer of the present invention.

FIG. 4 is a block diagram showing a fourth embodiment of the optical analyzer of the present invention. An optical analyzer 4 is different from the optical analyzer 1 in that the diagnostic light source section 10 of the optical analyzer 4 further includes a variable optical filter 18.

The variable optical filter 18 is provided between the lens 16 and the semi-transparent mirror 17, the transmission band thereof is variable, and a width of the transmission band is, for example, 1 nm. The diagnostic light source section 10 including such a variable optical filter 18 allows the variable optical filter 18 to selectively transmit light within a predetermined wavelength region from among broadband SC light output from the optical fiber 14, to output the transmitted light as diagnostic light. At this time, spectroscopes 31a and 31b included in the spectrum measurement section 30 may detect an acceptance optical power for each of transmission wavelengths at the variable optical filter 18. Accordingly, the configuration of the optical analyzer 4 of this embodiment can be simplified.

Embodiment of Medicine Sorting Method

Figure 5:
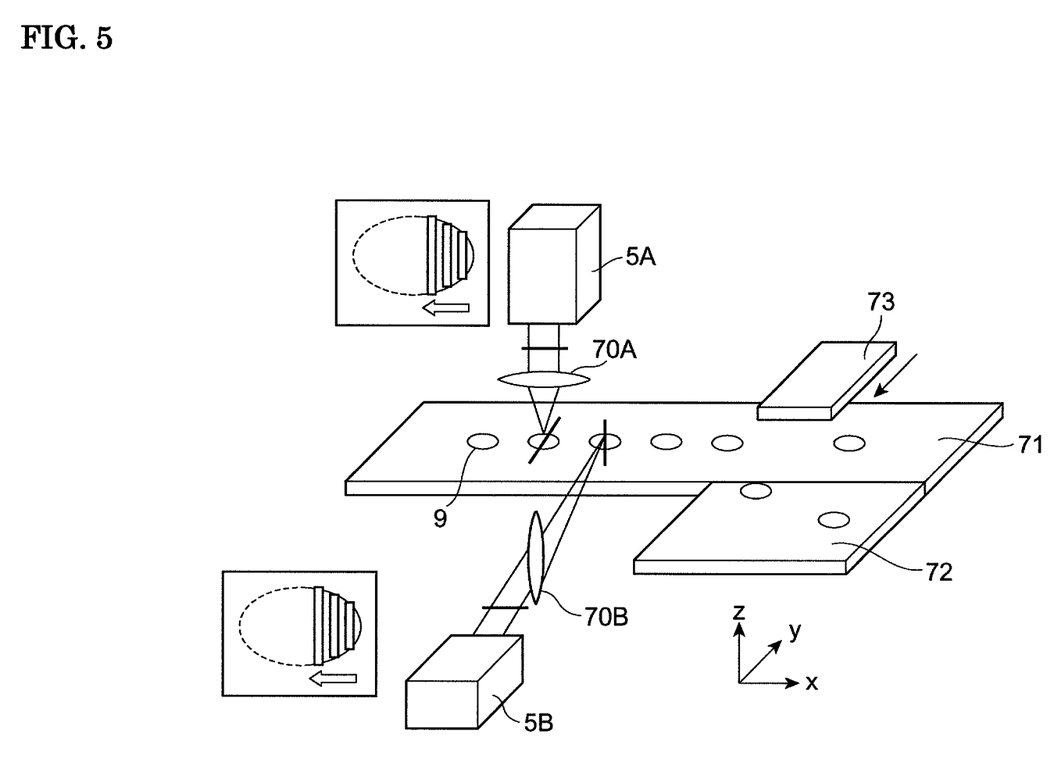
FIG. 5 is a schematic illustration showing an embodiment of a medicine sorting method of the present invention.

FIG. 5 is a schematic illustration showing an embodiment of a medicine sorting method of the present invention. A medicine sorting method in this embodiment includes using optical analyzers 5A and 5B of the present invention, measuring a spatial distribution of physiologically active molecules contained in medicine as a measurement subject, and determining whether the spatial distribution is conformed with a predetermined specification or not. Each of the optical analyzers 5A and 5B may be preferably the optical analyzer described in the third embodiment or an optical analyzer similar thereto. The optical analyzers 5A and 5B irradiates medicine 9 with diagnostic light in a z direction and a y direction. The medicine 9 as the measurement subject having the profile of a tablet is supplied by a belt conveyor 71. Herein, x represents a conveyance direction of the conveyor 71, z represents a direction orthogonal to the surface of the conveyor 71, and y represents a direction orthogonal to x and z.

The optical analyzer 5A emits diagnostic light in the z direction, the beam shape being elongated in the x direction, and the diagnostic light is converged at the medicine 9 by a lens 70A, the beam spot being elongated in the y direction. The optical analyzer 5B emits diagnostic light in the y direction, the beam shape being elongated in the x direction, and the diagnostic light is converged at the medicine 9 by a lens 70B, the beam spot being elongated in the z direction. As the belt conveyor 71 moves, the spot position on the medicine 9 is moved in the x direction.

Figure 6:
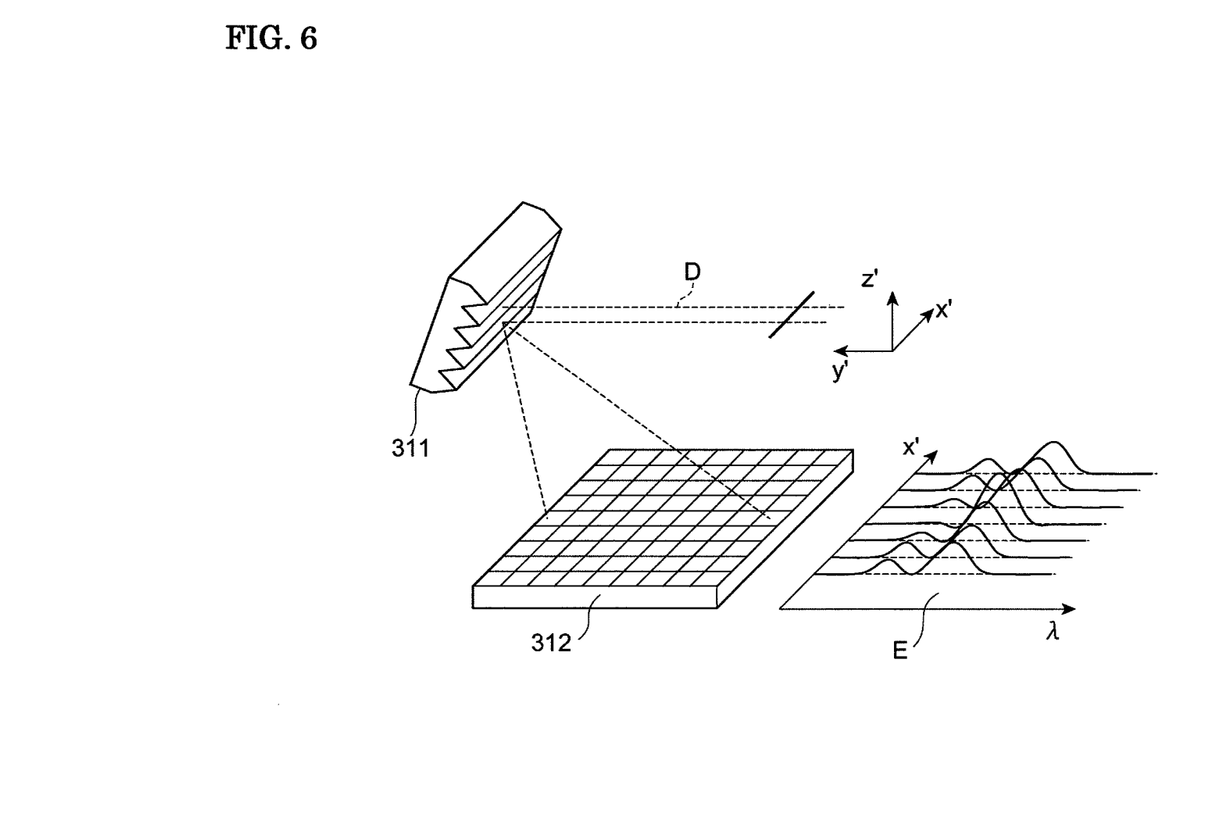
FIG. 6 is a schematic illustration showing an example of a spectroscope included in a spectrum measurement section of the optical analyzer of the present invention.

FIG. 6 is a schematic illustration showing an example of a spectroscope included in a spectrum measurement section of the optical analyzers 5A and 5B. Object light D having the beam shape being elongated in an x' direction and being propagated in a y' direction is input to the spectroscope, a diffraction grating 311 disperses the object light D in accordance with the wavelengths, and a two-dimensional array detector 312 receives the object light, so as to measure a power spectrum E of the object light D as a function of the position in the x' direction and its wavelength. As a result, the optical analyzers 5A and 5B measure component distributions of the medicine 9 projected on an x-y plane and an x-z plane. With these measurement results, it is determined whether the component distributions are conformed with a specification in which a component distribution is previously determined, and then not-conformed medicine is separated to another conveyor 72 by a pusher 73.

By using both the loss spectrum and the Raman spectrum as the optical analyzer of the third embodiment, specific components of medicine which contains various components may be separately measured. In a case where medicine contains a few kinds of components, merely one of the loss spectrum and the Raman spectrum may be used.

In the present invention, since the diagnostic light is emitted by the HE11 mode of the optical fiber 14, the diameter of the converged light on the medicine 9 may become as small as 1 μm at a minimum, thereby providing analysis of the component distribution with a high spatial resolution. In addition, by using the second diagnostic light with the wavelength longer than 800 nm and the first diagnostic light with the wavelength longer than 1400 nm, information of a deep portion of the medicine 9 can be obtained while reducing the influence of scattering, thereby eliminating the influence of fluorescence and providing a high signal-to-noise ratio. Further, by measuring the loss spectrum and the Raman spectrum at the same time, medicine containing various kinds of components can be measured.

Embodiment of Tissue Examination Method

Figure 7:
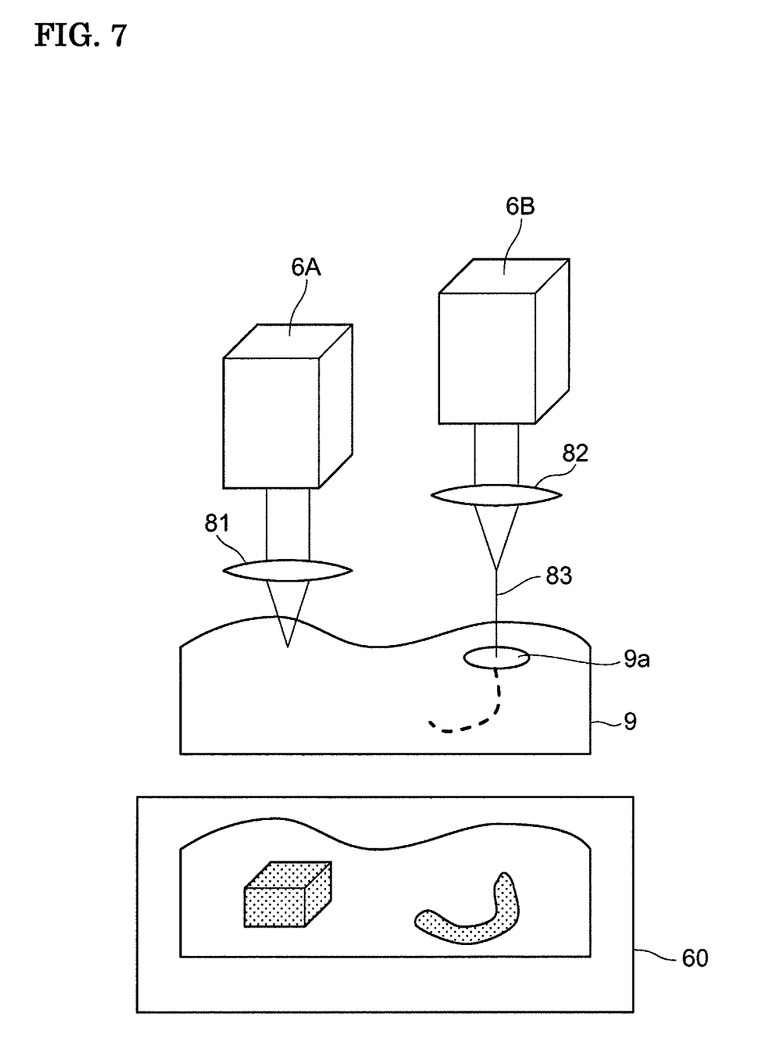
FIG. 7 is a schematic illustration showing an embodiment of a tissue examination method of the present invention.

FIG. 7 is a schematic illustration showing an embodiment of a tissue examination method of the present invention. The tissue examination method of this embodiment includes using optical analyzers 6A and 6B of the present invention, irradiating living tissue as a measurement subject with diagnostic light with a wavelength ranging from 1.6 to 1.8 μm, and measuring a spatial distribution of a physiologically active molecule contained in the measurement subject. The diagnostic light output from the optical analyzer 6A is converged by a lens 81 at the surface or the inside of living tissue 9 as the measurement subject. The optical analyzer 6A may be preferably the optical analyzer described in the third embodiment or an optical analyzer similar thereto. The optical analyzer 6A measures a distribution of physiologically active molecules such as enzyme, receptors, neurotransmitters, RNAs, or the like, contained in the living tissue 9, and displays the result on the image display section 60.

In addition, the diagnostic light output from the optical analyzer 6B may be converged at one end of an optical fiber 83 by a lens 82, and the optical fiber 83 may be inserted into the living tissue 9 from an incision portion 9a to irradiate the tissue with the diagnostic light in a manner like an endoscope, so that the distribution of the physiologically active molecules in the tissue may be measured. As described above, by measuring the distribution of the physiologically active molecules in the tissue, a disease may be diagnosed, and efficacy of a treatment may be evaluated.

Figure 8:
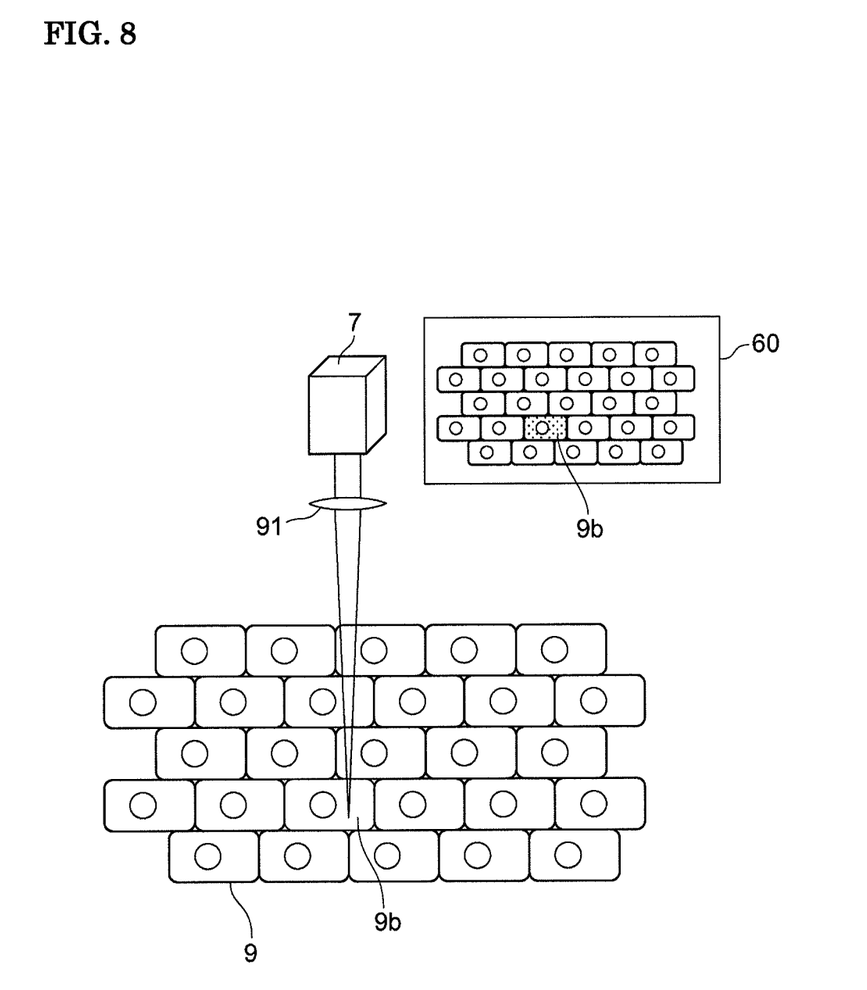
FIG. 8 is a schematic illustration showing another embodiment of the tissue examination method of the present invention.

FIG. 8 is a schematic illustration showing another embodiment of the tissue examination method of the present invention. This embodiment also uses an optical analyzer 7 of the present invention. Diagnostic light output from the optical analyzer 7 is converged by a lens 91 at the inside of living tissue 9 as a measurement subject. The tissue 9 is cultured from an undifferentiated embryonic stem cell 9b.

A frequency spectrum of the undifferentiated embryonic stem cell 9b is stored in the storage section 40 included in the optical analyzer 7. The optical analyzer 7 displays a portion conformed with the spectrum of the undifferentiated embryonic stem cell 9b on the display section 60. Since transplantation of the tissue 9 containing the undifferentiated embryonic stem cell 9b is known to have a risk of carcinogenesis, it is important to determine the presence of the undifferentiated embryonic stem cell 9b for securing the safety of transplantation of regenerated tissue.

This application is based on Japanese Patent Application (Patent Application No. 2006-13010) filed Jan. 20, 2006, the contents of which is hereby incorporated by reference.

INDUSTRIAL APPLICABILITY

The optical analyzer of the present invention may be preferably used for sorting medicine, examining living tissue, and the like, and is capable of performing analysis excellent in spatial resolution and in invasion depth.

The invention claimed is:
1. A method comprising:
outputting diagnostic light from a diagnostic light source section, the diagnostic light source section including a seed light source configured to output the seed light, and a silica optical fiber having a nonlinear optical coefficient of 20 $W^{-1}km^{-1}$ or more to which the seed light is input, wherein the diagnostic light source section is configured to generate supercontinuum light as diagnostic light having a HE11 mode field pattern utilizing a non- linear optical phenomenon within said silica optical fiber and output the diagnostic light;

converging the diagnostic light and irradiating a measurement subject with the diagnostic light;

acquiring object light generated at the measurement subject resulting from irradiation with the diagnostic light;

receiving the object light and measuring a frequency spectrum of the object light;

storing information of a frequency spectrum of a known substance; and calculating a correspondence between the frequency spectrum of the object light and the frequency spectrum of the known substance, and analyzing the measurement subject based on the correspondence, wherein a spatial density of an optical power is 1 mW/μm$^2$ or more at least at a part of the silica optical fiber of the diagnostic light source section, wherein the diagnostic light source section is configured to output the diagnostic light having an optical power of 1 μW/nm or more at least in a part of a spectrum band of wavelength from 0.8 to 3.0 μm, wherein the seed light source of the diagnostic light source section includes a pump pulse source, and in the diagnostic light source section, a spectrum of pump pulse light output from the pump pulse source is expanded utilizing the nonlinear optical phenomenon during propagation in the optical fiber so that the pump pulse light is output as the diagnostic light, wherein the step of acquiring object light further comprises acquiring, as the object light, diagnostic light having a loss generated at the measurement subject resulting from irradiation with the diagnostic light, wherein the frequency spectrum of the known substance contains a loss spectrum, and wherein the step of calculating the correspondence between the frequency spectrum of the object light and the frequency spectrum of the known substance further comprises calculating a correspondence between the frequency spectrum of the object light and the loss spectrum, and analyzing the measurement subject based on the correspondence.

2. The method according to claim 1, wherein the seed light source of the diagnostic light source section includes a seed pulse source and a pump source, in the diagnostic light source section, pump light output from the pump source is input to the silica optical fiber so as to generate an optical parametric gain in the silica optical fiber, and seed pulse light output from the seed pulse source is optically amplified using the optical parametric gain in the silica optical fiber and output as the diagnostic light, wherein a center wavelength of the diagnostic light is within a wavelength range from 1400 to 1800 nm, wherein the step of acquiring object light further comprises acquiring, as the object light, Raman scattering light generated at the measurement subject resulting from irradiation with the diagnostic light, wherein the frequency spectrum of the known substance further contains a Raman scattering spectrum, and wherein the step of calculating the correspondence between the frequency spectrum of the object light and the frequency spectrum of the known substance further comprises calculating a correspondence between the frequency spectrum of the object light and the Raman scattering spectrum, and analyzing the measurement subject based on the calculation result.

3. A medicine sorting method comprising the steps of:
using the method described in claim 1,
measuring a spatial distribution of physiologically active molecules contained in medicine as the measurement subject; and
determining whether the spatial distribution is conformed with a predetermined specification.

4. A tissue examination method comprising the steps of:
using the method described in claim 1,
irradiating living tissue as the measurement subject with diagnostic light with a wavelength within a wavelength range from 1.6 to 1.8 μm; and
measuring a spatial distribution of physiologically active molecules contained in the measurement subject.

5. An tissue examination method according to claim 4,
wherein information of the frequency spectrum of the known substance is information of a spectrum of an undifferentiated embryonic stem cell, and
wherein the undifferentiated embryonic stem cell contained in the measurement subject is detected.

6. A medicine sorting method according to claim 3,
wherein the seed light source of the diagnostic light source section includes a seed pulse source and a pump source, in the diagnostic light source section, pump light output from the pump source is input to the silica optical fiber so as to generate an optical parametric gain in the silica optical fiber, and seed pulse light output from the seed pulse source is optically amplified using the optical parametric gain in the silica optical fiber and output as the diagnostic light, wherein a center wavelength of the diagnostic light is within a wavelength range from 1400 to 1800 nm, wherein the step of acquiring object light further comprises acquiring, as the object light, Raman scattering light generated at the measurement subject resulting from irradiation with the diagnostic light, wherein the frequency spectrum of the known substance further contains a Raman scattering spectrum, and wherein the step of calculating the correspondence between the frequency spectrum of the object light and the frequency spectrum of the known substance further comprises calculating a correspondence between the frequency spectrum of the object light and the Raman scattering spectrum, and analyzing the measurement subject based on the correspondence.

7. A tissue examination method according to claim 4,
wherein the seed light source of the diagnostic light source section includes a seed pulse source and a pump source, in the diagnostic light source section, pump light output from the pump source is input to the silica optical fiber so as to generate an optical parametric gain in the silica optical fiber, and seed pulse light output from the seed pulse source is optically amplified using the optical parametric gain in the silica optical fiber and output as the diagnostic light, wherein a center wavelength of the diagnostic light is within a wavelength range from 1400 to 1800 nm, wherein the step of acquiring object light further comprises acquiring, as the object light, Raman scattering light generated at the measurement subject resulting from irradiation with the diagnostic light, wherein the frequency spectrum of the known substance further contains a Raman scattering spectrum, and wherein the step of calculating the correspondence between the frequency spectrum of the object light and the frequency spectrum of the known substance further comprises calculating a correspondence between the frequency spectrum of the object light and the Raman scattering spectrum, and analyzing the measurement subject based on the correspondence.

* * * * *